United States Patent
McGall et al.

(10) Patent No.: US 7,144,700 B1
(45) Date of Patent: Dec. 5, 2006

(54) PHOTOLITHOGRAPHIC SOLID-PHASE POLYMER SYNTHESIS

(75) Inventors: Glenn McGall, Mountain View, CA (US); Daniel E. Falvey, Takoma Park, MD (US); Jacqueline A. Fidanza, Mountain View, CA (US); Brian M. Feldman, Pittsford, NY (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/620,780

(22) Filed: Jul. 21, 2000

Related U.S. Application Data

(60) Provisional application No. 60/146,574, filed on Jul. 30, 1999, provisional application No. 60/145,402, filed on Jul. 23, 1999.

(51) Int. Cl.
- C12Q 1/68 (2006.01)
- C12M 1/34 (2006.01)
- C07H 21/00 (2006.01)
- G01N 33/543 (2006.01)

(52) U.S. Cl. .......................... 435/6; 435/4; 435/283.1; 435/287.8; 435/DIG. 40; 435/DIG. 42; 435/DIG. 49; 436/518; 436/524; 436/527; 436/106; 436/145; 536/25.3; 536/25.31; 536/25.32; 536/25.33; 536/25.34

(58) Field of Classification Search .................. 435/7.1, 435/7.2, DIG. 42, DIG. 49; 436/518; 530/333, 530/334; 536/25.3, 25.31, 25.32, 25.33, 536/25.34
See application file for complete search history.

(56) References Cited

U.S. PATENT DOCUMENTS

| | | | |
|---|---|---|---|
| 4,554,238 A * | 11/1985 | Bushman ..................... 430/258 |
| 5,143,854 A * | 9/1992 | Pirrung et al. .............. 435/6 |
| 5,242,974 A | 9/1993 | Holmes ..................... 525/54.11 |
| 5,252,743 A | 10/1993 | Barrett et al. ............ 548/303.7 |
| 5,288,514 A | 2/1994 | Ellman .......................... 427/2 |
| 5,324,633 A | 6/1994 | Fodor et al. ..................... 435/6 |
| 5,384,261 A | 1/1995 | Winkler et al. ............. 436/518 |
| 5,405,783 A | 4/1995 | Pirrung et al. .............. 436/518 |
| 5,412,087 A * | 5/1995 | McGall et al. ............. 536/24.3 |
| 5,424,186 A * | 6/1995 | Fodor et al. ..................... 435/6 |
| 5,445,934 A | 8/1995 | Fodor et al. ..................... 435/6 |
| 5,451,683 A | 9/1995 | Barrett et al. ............ 548/302.7 |
| 5,482,867 A | 1/1996 | Barrett et al. ............... 436/518 |
| 5,489,678 A | 2/1996 | Fodor et al. ................. 536/22.1 |
| 5,491,074 A | 2/1996 | Aldwin et al. ............. 435/69.7 |
| 5,510,270 A | 4/1996 | Fodor et al. ................. 435/518 |
| 5,527,681 A | 6/1996 | Holmes .......................... 435/6 |
| 5,541,061 A | 7/1996 | Fodor et al. ..................... 435/6 |
| 5,550,215 A | 8/1996 | Holmes ....................... 530/334 |
| 5,571,639 A | 11/1996 | Hubbell et al. ................ 430/5 |
| 5,593,839 A | 1/1997 | Hubbell et al. ................ 435/6 |
| 5,599,695 A | 2/1997 | Pease et al. ............... 435/91.1 |
| 5,624,711 A | 4/1997 | Sundberg et al. ........... 427/261 |
| 5,631,734 A | 5/1997 | Stern et al. ................. 356/317 |
| 5,639,603 A | 6/1997 | Dower et al. ................... 435/6 |
| 5,677,195 A | 10/1997 | Winkler et al. ............. 436/518 |
| 5,744,101 A | 4/1998 | Fodor et al. ................. 422/131 |
| 5,744,305 A | 4/1998 | Fodor et al. ..................... 435/6 |
| 5,753,788 A | 5/1998 | Fodor et al. ............... 536/22.1 |
| 5,770,358 A | 6/1998 | Dower et al. ................... 435/6 |
| 5,770,456 A | 6/1998 | Holmes ....................... 436/518 |
| 5,831,070 A | 11/1998 | Pease et al. ............... 536/25.3 |
| 5,856,011 A | 1/1999 | Sogabe ....................... 428/411.1 |
| 5,902,714 A * | 5/1999 | Reimers ..................... 430/287.1 |
| 6,022,963 A | 2/2000 | McGall et al. ............. 536/25.3 |
| 6,083,697 A * | 7/2000 | Beecher et al. ................ 435/6 |
| 6,271,957 B1 * | 8/2001 | Quate et al. ................ 359/298 |

FOREIGN PATENT DOCUMENTS

| WO | 89/10977 | 11/1989 |
| WO | 89/11548 | 11/1989 |

OTHER PUBLICATIONS

Webster's II New Riverside Dictionary (Riverside Publishing: 1994) p. 766 (definition of "monomer").*

Banerjee et al., "Protecting group release through photoinduced electron transfer: Wavelength control through sensitized irradiation", Tetrahedron Letters, Jun. 25, 1998, 39(26), pp. 4335-4638.*

Banerjee et al., "Protecting Groups That Can Be Removed through Photochemical Electron Transfer: Mechanistic and Product Studies on Photosensitized Release of Carboxylates from Phenacyl Esters", J. Organic Chemistry, Sep. 5, 1997, 62(18), pp. 6245-6251.*

Nishida et al., "Hydrolysis of tosyl esters initiated by an electron transfer from photoexcited electron-rich aromatic compounds", J. Organic Chemistry, Jul. 8, 1988, 53(14), pp. 3386-3387.*

(Continued)

Primary Examiner—Peter Paras, Jr.
Assistant Examiner—My-Chau T Tran
(74) Attorney, Agent, or Firm—Affymetrix, Inc.

(57) ABSTRACT

Methods, employing a polycyclic hydrocarbon or a polycyclic heteroaromatic compound as sensitizers, are provided to increase the efficiency of removing, by irradiation, photolabile protecting groups that mask reactive sites on synthesis intermediaries. Preferred groups of photolabile protecting moieties include: ((α-methyl-2-nitropiperonyl)-oxy)carbonyl (MeNPOC), ((Phenacyl)-oxy)carbonyl (PAOC), O-(9-phenylxanthen-9-yl) (PIXYL), and ((2-methylene-9,10-anthraquinone)-oxy)carbonyl (MAQOC). In conjunction with using the sensitizers and protecting groups described above, a method of forming, from component molecules, a plurality of compounds on a support, each compound occupying a separate predefined region of the support is provided. These resulting solid-phase arrays are useful, for example, to assay for the presence of biochemical products in biological samples.

9 Claims, 2 Drawing Sheets

OTHER PUBLICATIONS

Amit, B., et al., "Photosensitive protecting groups of amino sugars and their use in glycoside synthesis. 2-nitrobenzyloxycarbonylamino and 6-nitroveratryloxycarbonylamino derivatives", *J. Org. Chem.*, 39, pp. 192-196, (1974).

Banerjee, A., et al., "Protecting Group Release Through Photoinduced Electron Transfer: Wavelength Control Through Sensitized Irradiation", *Tetrahedron Letters*, 39, pp. 4635-4638, (1998).

Banerjee, A., et al., "Protecting Groups That Can Be Removed Through Photochemical Electron Transfer: Mechanistic and Product Studies on Photosensitized Release of Carboxylates from Phenacyl Esters", *J. Org. Chem.*, 62, pp. 6245-6251, (1997).

Chaiken, I.M., "Semisynthetic Peptides and Proteins", *In: CRC Critical Reviews in Biochemistry*, 11 (3), pp. 255-301, (Sep. 1981).

Cho, C.Y., et al., "An Unnatural Biopolymer", *Science*, 261, pp. 1303-1305, (Sep. 1993).

Fodor, S.P., et al., "light-Directed, Spatially Addressable Parallel Chemical Synthesis", *Science*, 251, pp. 767-773, (Feb. 1991).

Furuta, T., et al., "Photochemical Properties of New Photolabile cAMP Derivatives in a Physiological Saline Solution", *J. Org. Chem.*, 60, pp. 3953-3956, (1995).

Gutte, B., et al., "The Total Synthesis of an Enzyme with Ribonuclease A Activity", *Journal of the American Chemical Society*, 91 (2), pp. 501-502, (Jan. 1969).

Kaiser, E.T., et al., "Peptide and Protein Synthesis by Segment Synthesis-Condensation", *Science*, 243, pp. 187-192, (Jan. 1989).

Kent, S.B., "Chemical Synthesis of Peptides and Proteins", *Ann. Rev. Biochem.*, 57, pp. 957-989, (1988).

McCray, J.A., et al., "Properties and Uses of Photoreactive Caged Compounds", *Annu. Rev. Biophys. Biophys. Chem.*, 18, pp. 239-270. (1989).

McGall, G.H., et al., "The Efficiency of Light-Directed Synthesis of DNA Arrays on Glass Substrates", *Journal of the American Chemical Society*, 119 (22), pp. 5081-5090. (Jun. 4, 1997).

Merrifield, B., "Solid Phase Synthesis", *Science*, 232, pp. 341-347, (Apr. 1986).

Merrifield, R.B., "Solid Phase Peptide Synthesis—1. The Synthesis of a Tetrapeptide", *J. Am. Chem. Soc.*, 85, pp. 2149-2154, (Jul. 20, 1963).

Misetic, A., et al., "The Pixyl (Px) Group: A Novel Photocleavable Protecting Group for Primary Alcohols", *Tetrahedron Letters*, 39, pp. 1653-1656, (1998).

Patchornik, "Photosensitive Protecting Groups", *J. Am. Chem. Soc.*, 92, pp. 6333-6335, (1970).

\* cited by examiner ((α-Methyl-2-nitropiperonyl)-oxy)carbonyl
MeNPOC

(Phenacyl)-oxy)carbonyl
PAOC

O-(9-Phenylxanthen-9-yl
PIXYL

((2-Methylene-9,10-anthraquinone)-
oxy)carbonyl
MAQOC

9,10-Dimethylanthracene
dMA

9-Methylcarbazole
9MC

PHOTOLITHOGRAPHIC SOLID-PHASE POLYMER SYNTHESIS

CROSS REFERENCE TO RELATED APPLICATIONS

This application claims priority to U.S. Provisional Patent Application Ser. No. 60/145,402 filed Jul. 23, 1999, and Ser. No. 60/146,574, filed Jul. 30, 1999, the disclosures of which are incorporated herein by reference in their entirety.

TECHNICAL FIELD

This invention relates to the preparation of polymers on a substrate. Accordingly, this invention covers the general fields of organic chemistry, biochemistry, and molecular biology among others.

BACKGROUND OF THE INVENTION

The present invention concerns the synthesis and placement of polymers at known locations on a substrate. The collection of all the polymers on a substrate is known as an array. The methods described may be applied, for example, to create solid-phase sources of chemical diversity, such as arrays of peptides, oligosaccharides, polymeric nucleic acid, etc., on a substrate, for use in screening for biological activity.

The preferred means for preparing arrays employs radiation-labile protecting groups and photolithographic masks to achieve spatially defined combinatorial polymer synthesis on a substrate surface. One preferred prior technique is shown in U.S. Pat. No. 5,143,854, which is incorporated by reference in its entirety for all purposes. Using photolithographic techniques for preparing solid-phase polymer arrays have met with considerable success. Nonetheless, it is desirable to meet a level of 100% efficiency. It would be beneficial therefore, to develop faster methods with greater yields (with minimal or no highly reactive byproducts) to make the current photochemical polymer synthetic processes more efficient and economical.

SUMMARY OF THE INVENTION

According to the present invention, methods are provided to synthesize polymer arrays on a substrate by incorporating compounds with photocleavable protecting groups, wherein the photocleavable protecting groups can be removed by photolysis in the presence of one or more sensitizing agents, to unmask a reactive group. The photocleavable protecting group can be selected from the group consisting of an aromatic acyl group, a nitroaromatic group, and a polycyclic heteroaromatic group. The sensitizing agent may be selected from the group consisting of a polycyclic hydrocarbon and a polycyclic heteroaromatic compound.

Preferred groups of photocleavable protecting groups include: ((α-methyl-2-nitropiperonyl)-oxy)carbonyl (MeNPOC), ((Phenacyl)-oxy)carbonyl (PAOC), O-(9-phenylxanthen-9-yl) (PIXYL), and ((2-methylene-9,10-anthraquinone)-oxy)carbonyl (MAQOC). Preferred sensitizing agents include 9,10-dimethylanthracene (dMA) and 9-methylcarbazole (9MC). Some preferred compounds having photocleavable protecting groups are 5'-X-2'-deoxythymidine-2-cyanoethyl-3'-N,N-diisopropyl-phosphoramidites, where X is the photolabile protecting group.

A further understanding of the nature and advantages of the methods herein may be realized by reference to the remaining portions of the specification and the attached data and figures.

DETAILED DESCRIPTION OF THE INVENTION

A. General

Figure 1:
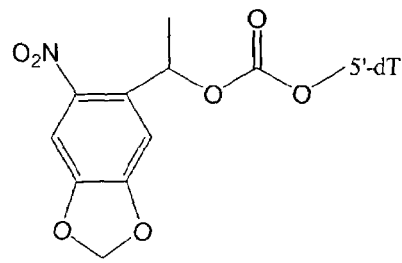
FIG. 1 shows some of the photocleavable protecting groups and sensitizing agents of the present invention.
Figure 1:
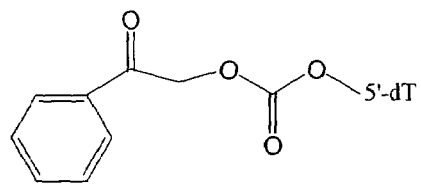
Figure 1:
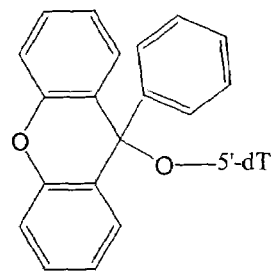
Figure 1:
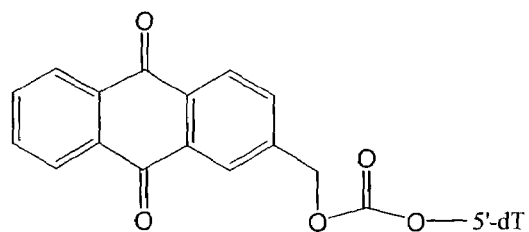
Figure 1:
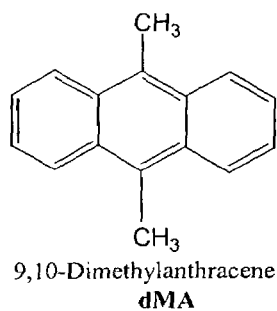
Figure 1:
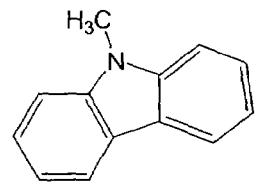

One approach to achieve the synthesis of intended polymers, each within a predefined region on a substrate, is the ability to mask certain reactive sites with a protecting group, while other unmasked reactive sites allow coupling between component molecules. The present invention describes a means for attaching photoremovable protecting groups to the surface of a substrate, exposing selected regions of the substrate to light to activate those regions, attaching a monomer with a photoremovable group to the activated regions, and repeating the steps of activation and attachment until polymers of the desired length and sequences are synthesized.

There are a number of advantages of using photolabile protecting groups in the synthesis of solid-phase arrays. First, irradiation can occur from the front-side or through the backside of the substrate. Second, a number of photolabile protecting groups are known. Third, photolabile protecting groups enable specific sites of interest on the surface to be spatially addressed by irradiation with light at the appropriate wavelength through a photolithographic mask. However, an undesirable side effect of using irradiation for lysis of photolabile protecting groups on a solid support is the low-level generation of deprotected moieties that are non-reactive, or dead-end, photo byproducts. Such byproducts may accumulate at each step of an overall synthesis in which irradiation is used, and consequently result in considerable loss of polymer yield. According to the present invention, a method is provided to improve coupling efficiencies, by inclusion of one or more sensitizing agents during a deprotection step as part of an overall synthesis, to result in improved polymer recovery.

Techniques for large-scale polymer synthesis, and methods applicable to the array synthesis of polymers have been described in U.S. Pat. Nos. 5,143,854, 5,242,974, 5,252,743, 5,324,663, 5,384,261, 5,405,783, 5,412,087, 5,424,186, 5,445,934, 5,451,683, 5,482,867, 5,489,678, 5,491,074, 5,510,270, 5,527,681, 5,550,215, 5,571,639, 5,593,839, 5,599,695, 5,624,711, 5,631,734, 5,677,195, 5,744,101, 5,744,305, 5,753,788, 5,770,456, 5,831,070, and 5,856,011, all incorporated herein by reference in their entirety for all purposes.

B. Definitions

The following definitions are set forth to illustrate and define the meaning and scope of the terms used to describe the invention herein. U.S. Pat. No. 5,445,934 and the pending patent application Ser. No. 08/812,005, both incorporated by reference in their entirety for all purposes, are to be used as sources for the definitions of terms not defined below.

An "array" is an intentionally created collection of differing molecules which can be prepared either synthetically or biosynthetically and screened for biological activity in a variety of different formats (e.g., libraries of soluble molecules; and libraries of compounds tethered to resin beads, silica chips, or other solid supports). The term is also intended to refer to an intentionally created collection of stereoisomers.

"Predefined region" refers to a localized area on a solid support that is, or was, intended to be used for formation of a selected molecule and is otherwise referred to herein in the alternative as a "selected" region. The predefined region may have any convenient shape, e.g., circular, rectangular, elliptical, wedge-shaped, etc. For the sake of brevity herein, "predefined regions" are sometimes referred to simply as "regions" or "known locations." In some embodiments, a predefined region, and therefore the area upon which each distinct compound is synthesized, can be smaller than about 1 cm$^2$, or even as small as 1 µm$^2$ as shown in the patents cited above, or any increment in between. Within these regions, the molecule synthesized therein is preferably synthesized in a substantially pure form. In additional embodiments, a predefined region can be achieved by physically separating the regions (i.e., beads, resins, gels, etc.) into wells, trays, etc.

"Solid support", "support", and "substrate" refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See the above patents for a broader list of supports.

A "protective group" is a moiety which is bound to a molecule and which may be spatially removed upon selective exposure to an activator such as electromagnetic radiation. Several examples of protective groups are known in the literature and will become evident upon further reading of the present disclosure. Other examples of activators include ion beams, electric fields, magnetic fields, electron beams, x-ray, and the like.

"Activating group" refers to those groups which, when attached to a particular functional group or reactive site, render that site more reactive toward covalent bond formation with a second functional group or reactive site. For example, the group of activating groups which can be used in the place of a hydroxyl group include —O(CO)Cl; —OCH$_2$Cl; —O(CO)OAr, where Ar is an aromatic group, preferably, a p-nitrophenyl group; —O(CO)(ONHS); and the like. The group of activating groups which are useful for a carboxylic acid include simple ester groups and anhydrides. The ester groups include alkyl, aryl and alkenyl esters and in particular such groups as 4-nitrophenyl, N-hydroxylsuccinimide and pentafluorophenol. Other activating groups are known to those of skill in the art.

A "channel block" is a material having a plurality of grooves or recessed regions on a surface thereof. The grooves or recessed regions may take on a variety of geometric configurations, including but not limited to stripes, circles, serpentine paths, or the like. Channel blocks may be prepared in a variety of manners, including etching silicon blocks, molding or pressing polymers, etc.

The terms "photolabile", "photoremovable" and "photocleavable" are used interchangeably throughout this application.

The term "heteroaromatic" refers to an aromatic monovalent mono- or poly-cyclic radical having at least one heteroatom within the ring, e.g., nitrogen, oxygen or sulfur, wherein the aromatic ring can optionally be mono-, di- or tri-substituted, independently, with alkyl, lower-alkyl, cycloalkyl, hydroxylower-alkyl, aminolower-alkyl, hydroxyl, thiol, amino, halo, nitro, lower-alkylthio, lower-alkoxy, mono-lower-alkylamino, di-lower-alkylamino, acyl, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoly, carbamoyl, lower-alkylcarbamoyl, and di-lower-alkylcarbamoyl. Further the term also includes instances where a heteroatom within the ring has been oxidized, such as, for example, to form an N-oxide or sulfone.

For example, heteroaryl radicals with one or more nitrogen atoms are tetrazoly, pyridyl (e.g., 4-pyridyl, 3-pyridyl, 2-pyridyl), pyrrolyl (e.g., 2-pyrrolyl, 2-(N-alkyl)pyrrolyl), pyridazinyl, quinolyl (e.g., 2-quinolyl, 3-quinolyl etc.), imidazolyl, isoquinolyl, pyrazolyl, pyrazinyl, pyrimidinyl, pyridonyl or pyridazinony.

Some heteroaryl radicals with an oxygen atom are 2-furyl, 3-furyl or benzofuranyl. Some sulfur containing heteroaryl radicals are thienyl, and benzothienyl. Some mixed heteroatom heteroaryl radicals are furazanyl and phenothiazinyl.

The term "optionally substituted" refers to the presence or lack thereof of a substituent on the group being defined.

The term "compound" as used herein in the context of forming compounds on a substrate refers to either a single compound (i.e., a single monomer) attached to a support or a nascent polymer or a partially completed polymer.

The term "molecule" ordinarily refers to a monomer that is the building block in forming a compound or a polymer as the context indicates. However, one of skill in the art will recognize that the protecting groups disclosed herein can also be attached to species not traditionally considered as "molecules". Therefore, compositions such as solid surfaces (e.g., paper, nitrocellulose, glass, polystyrene, silicon, modified silicon, GaAs, silica and the like), gels (e.g., agarose, sepharose, polyacrylamide and the like) to which the protecting groups disclosed herein are attached are also contemplated by this invention.

Molecules can also include more than one monomer. As units or building blocks for a polymer, molecules include dimers, trimers, etc. to make a larger polymer. Such building blocks in forming a compound or a polymer include amino acids, peptides, polypeptides, nucleic acids, nucleotides, nucleosides, monosaccharides, and the like. Preferred nucleosides are ribonucleosides and deoxyribonucleosides such as adenosine, deoxyadenosine, cytidine, deoxycytidine, thymidine, uracil, guanosine and deoxyguanosine as well as oligonucleotides incorporating such nucleosides. Preferably, the building block is linked to the photolabile protecting group via a hydroxy or amine group.

C. The Methods

The present invention concerns with methods to synthesize polymer arrays on a substrate. The methods primarily involve "light-directed methods" incorporating compounds with photocleavable protecting groups and sensitizing agents. "Light-directed" methods (which are one technique in a family of methods known as VLSIPS™ methods) are described in U.S. Pat. No. 5,143,854 ('854), which is incorporated by reference. By using the lithographic techniques disclosed herein, it is possible to direct light to relatively small and precisely known locations on the substrate. It is, therefore, possible to synthesize polymers of a known chemical sequence at known locations on the substrate The light directed methods discussed in the '854 patent involve activating predefined regions of a substrate or solid support and then contacting the substrate with a preselected monomer solution. The predefined regions can be activated with a light source, typically shown through a mask (much in the manner of photolithography techniques used in integrated circuit fabrication). Other regions of the substrate remain inactive because they are blocked by the mask from illumination and remain chemically protected. Thus, a light pattern defines which regions of the substrate react with a given monomer. By repeatedly activating different sets of predefined regions and contacting different monomer solutions with the substrate, a diverse array of polymers is produced on the substrate. Of course, other steps such as washing unreacted monomer solution from the substrate can be used as necessary.

Thus, in the light-directed polymer synthesis, the photocleavable protecting groups are removed by photolysis to unmask a reactive group. The photocleavable protecting group can be any of the many known groups. In some aspects, the photocleavable protecting group may be selected from the group consisting of an aromatic acyl group, a nitroaromatic group, and a polycyclic heteroaromatic group. The sensitizing agent is a chemical compound selected from the group consisting of a polycyclic hydrocarbon compound and a polycyclic heteroaromatic compound.

Some preferred groups of photocleavable protecting groups include: ((α-methyl-2-nitropiperonyl)-oxy)carbonyl (MeNPOC), ((Phenacyl)-oxy)carbonyl (PAOC), O-(9-phenylxanthen-9-yl) (PIXYL), and ((2-methylene-9,10-anthraquinone)-oxy)carbonyl (MAQOC). Some preferred sensitizing agents include 9,10-dimethylanthracene (dMA) and 9-methylcarbazole (9MC). These groups and sensitizing agents are shown in FIG. 1. Some preferred compounds having photocleavable protecting groups are 5'-X-2'-deoxythymidine-2-cyanoethyl-3'-N,N-diisopropyl-phosphoramidites, where X is the photolabile protecting group.

In one aspect, a method of attaching a molecule with a reactive site to a support is provided wherein the method comprises the steps of:
  (a) providing a support with a reactive site;
  (b) binding a first molecule to the reactive site, said first molecule comprising a masked reactive site attached to a photolabile protecting group selected from the group consisting of MeNPOC, PAOC, PIXYL, or MAQOC, to produce a derivatized support having immobilized thereon the molecule attached to the photolabile protecting group; and
  (c) removing the photolabile protecting group in the presence of a sensitizing agent to provide a derivatized support comprising the molecule with an unmasked reactive site immobilized thereon.

The method further comprises the steps of
  (d) coupling a second molecule to the unmasked reactive site, which second molecule comprises a second masked reactive site attached to the photolabile protecting group to produce a derivatized support having immobilized thereon a chain of the first and second molecules; and
  (e) removing the photolabile protecting group in the presence of a sensitizing agent to provide a derivatized support with a chain of the first and second molecules with a second unmasked reactive site immobilized thereon.

The sensitizing agent is selected from the group consisting of dMA and 9MC.

As one skilled in the art will recognize, the process can be repeated to generate a compound comprising a chain of component molecules attached to the solid support. The above method thus further comprises repeating steps (d) and (e) with a succession of molecules to provide a chain of molecules immobilized on the support.

In a "mix and match" approach, the photolabile protecting groups may be varied at different steps in the process depending on the ease of synthesis of the precursor molecule. Alternatively, photolabile protecting groups can be used in some steps of the synthesis and chemically labile groups can be used in other steps.

The method can also be generalized to prepare, from component molecules (or monomers), a plurality of polymers on a support, each polymer occupying a separate predefined region of the support, wherein the method comprises the steps of:
  (a) activating a region of the support;
  (b) binding a molecule to the first region, said molecule comprising a masked reactive site linked to a photolabile protecting group selected from the group consisting of MeNPOC, PAOC, PIXYL, or MAQOC,
  (c) repeating steps (a) and (b) on other regions of the support whereby each of said other regions has bound thereto another molecule comprising a masked reactive site linked to the photolabile protecting group, wherein said another molecules may be the same or different from that used in step (b);
  (d) removing the photolabile protecting group from one of the molecules bound to one of the regions of the support in the presence of a sensitizing agent, either dMA and 9MC, to provide a region bearing a molecule with an unmasked reactive site;
  (e) binding an additional molecule to the molecule with an unmasked reactive site;
  (f) repeating steps (d) and (e) on regions of the support until a desired plurality of polymers is formed from the component molecules, each polymer occupying separate regions of the support.

The method further comprises the steps of:
  (g) covalently binding a second molecule comprising a masked reactive site linked to a chemically labile protecting group to a reactive site, wherein the reactive site is either on an activated region of the support as formed in step (a) or is an unmasked reactive site on a molecule on the support as formed in step (d);
  (h) replacing the chemically labile protecting group with the photolabile protecting group to provide a region of the support having a molecule with the photolabile protecting group; and
  (i) repeating steps (d)–(f) of the above steps as desired.

Thus, the methods can be practiced to prepare an array of any polymer. Preferable biological polymers include nucleic acids, peptides and carbohydrates.

A related method of forming, from component molecules, a plurality of polymers on a support, each polymer occupying a separate predefined region of the support, is also provided. Briefly, the method comprises the steps of:

(a) activating a region of the support;
(b) binding a molecule to the first region, said molecule comprising a masked reactive site linked to a photolabile protecting group described above;
(c) repeating steps (a) and (b) on other regions of the support whereby each of said other regions has bound thereto another molecule comprising a masked reactive site linked to the photolabile protecting group, wherein said another molecules may be the same or different from that used in step (b);
(d) removing, by irradiation and in the presence of a sensitizing agent described above, the photolabile protecting group from one of the molecules bound to one of the regions of the support to provide a region bearing a molecule with an unmasked reactive site;
(e) binding an additional molecule to the molecule with an unmasked reactive site;
(f) repeating steps (d) and (e) on regions of the support until a desired plurality of polymers is formed from the component molecules, each polymer occupying separate regions of the support.

By using the methods of this invention, polymer arrays of varying sizes can be prepared. For example, arrays of $10^6$ to $10^{12}$ or more of different or identical polymers can be prepared.

As discussed above, in some steps, chemically labile protecting groups can be used instead of the photolabile protecting groups in a "mix and match" approach. When so used, the replacement is accomplished by removing the chemically labile protecting groups under conditions which do not affect any photolabile protecting groups that may be on the support. This may be particularly advantageous when the monomers are more readily available carrying chemically labile protecting groups than the photolabile protecting groups described herein.

Chemically labile protecting groups can be deprotected by using chemicals (for example acids or bases) that are in a liquid or vapor phase. Further, the chemical deprotection can be carried out either at or below atmospheric pressures. Such vapor phase deprotection has been disclosed in the U.S. Pat. Nos. 5,599,695, and 5,831,070 and in the copending application Ser. No. 09/093,843, filed May 22, 1998, which are incorporated by reference.

It will be recognized that any method of forming a chain of compounds or an array of polymers on a support using in at least one step a protecting group/reagent or compound and deprotecting a photolabile group in the presence of a sensitizing agent as described herein is within the scope of this invention.

A method of forming, from component molecules, a plurality of compounds on a support, each compound occupying a separate predefined region of the support, is, provided, wherein the method comprises the steps of:
(a) activating a region of the support;
(b) binding a molecule to the first region, said molecule comprising a masked reactive site linked to a protecting group;
(c) repeating steps (a) and (b) on other regions of the support whereby each of said other regions has bound thereto another molecule comprising a masked reactive site linked to a protecting group, wherein said another molecules and protecting groups can be the same or different to each other;
(d) removing the protecting group from one of the molecules bound to one of the regions of the support in the presence of a sensitizing agent described above to provide a region bearing a molecule with an unmasked reactive site;
(e) binding an additional molecule to the molecule with an unmasked reactive site;
(f) repeating steps (d) and (e) on regions of the support, until a desired plurality of compounds is formed from the component molecules, each compound occupying separate regions of the support, with the proviso that at least one of the protecting groups used in steps (a)–(f) is a photolabile protecting group described above.

In some aspects, the binding step of the above methods forms a covalent linkage.

In some aspects, the "molecule" in the methods described above is a nucleoside or a deoxynucleoside or an analog thereof. When nucleotides and oligonucleotide compositions are used, with the protecting groups of this invention, the protecting groups are preferably incorporated into the 3'-OH or the 5'-OH of the nucleoside. Other preferred compounds are protected peptides, proteins, oligonucleotides and oligodeoxyribonucleotides. Small organic molecules, proteins, hormones, antibodies and other such species having nucleophilic reactive groups can be protected using the protecting groups disclosed herein.

The terms nucleoside, nucleotide, deoxynucleoside and deoxynucleotide generally include analogs such as those described herein. These analogs are those molecules having some structural features in common with a naturally occurring nucleoside or nucleotide such that when incorporated into an oligonucleotide or oligonucleoside sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

Analogs also include protected and/or modified monomers as are conventionally used in oligonucleotide synthesis. As one of skill in the art is well aware oligonucleotide synthesis uses a variety of base-protected deoxynucleoside derivatives in which one or more of the nitrogens of the purine and pyrimidine moiety are protected by groups such as dimethoxytrityl, benzyl, tert-butyl, isobutyl and the like. Specific monomeric building blocks that are encompassed by this invention include base protected deoxynucleoside H-phosphonates and deoxynucleoside phosphoramidites.

For instance, structural groups are optionally added to the ribose or base of a nucleoside for incorporation into an oligonucleotide, such as a methyl, propyl or allyl group at the 2'-O position on the ribose, or a fluoro group which substitutes for the 2'-O group, or a bromo group on the ribonucleoside base. 2'-O-methyloligoribonucleotides (2'-O-MeORNs) have a higher affinity for complementary nucleic acids (especially RNA) than their unmodified counterparts. 2'-O-MeORNA phosphoramidite monomers are available commercially, e.g., from Chem Genes Corp. or Glen Research, Inc. Alternatively, deazapurines and deazapyrimidines in which one or more N atoms of the purine or pyrimidine heterocyclic ring are replaced by C atoms can also be used.

The phosphodiester linkage, or "sugar-phosphate backbone" of the oligonucleotide analogue, can also be substituted or modified, for instance with methyl phosphonates or O-methyl phosphates. Another example of an oligonucleotide analogue for purposes of this disclosure includes "peptide nucleic acids" in which a polyamide backbone is attached to oligonucleotide bases, or modified oligonucleotide bases. Peptide nucleic acids which comprise a polyamide backbone and the bases found in naturally occurring nucleosides are commercially available from, e.g., Biosearch, Inc. (Bedford, Mass.).

Nucleotides with modified bases can also be used in this invention. Some examples of base modifications include 2-aminoadenine, 5-methylcytosine, 5-(propyn-1-yl)cytosine, 5-(propyn-1-yl)uracil, 5-bromouracil, and 5-bromocytosine which can be incorporated into oligonucleotides in order to increase binding affinity for complementary nucleic acids. Groups can also be linked to various positions on the nucleoside sugar ring or on the purine or pyrimidine rings which may stabilize the duplex by electrostatic interactions with the negatively charged phosphate backbone, or through hydrogen bonding interactions in the major and minor groves. For example, adenosine and guanosine nucleotides can be substituted at the $N^2$ position with an imidazolyl propyl group, increasing duplex stability. Universal base analogues such as 3-nitropyrrole and 5-nitroindole can also be included. A variety of modified oligonucleotides and oligonucleotide analogs suitable for use in this invention are described in, e.g., "Antisense Research and Application", S. T. Crooke and B. LeBleu (eds.) (CRC Press, 1993) and "Carbohydrate Modifications in Antisense Research" in ACS Symp. Ser. #580, Y. S. Sanghvi and P. D. Cook (eds.) ACS, Washington, D.C. 1994).

In some preferred aspects, contrast between features may be enhanced through the front side exposure of the substrate. Front side exposure is described in the U.S. application Ser. No. 08/634,053, filed Apr. 17, 1996, which is incorporated by reference.

Isolation and purification of the compounds and intermediates described herein can be effected, if desired, by any suitable separation or purification procedure such as, for example, filtration, extraction, crystallization, column chromatography, thin-layer chromatography, thick-layer (preparative) chromatography, distillation, or a combination of these procedures. Specific illustrations of suitable separation and isolation procedures can be had by reference to the example herein below. However, other equivalent separation or isolation procedures can, of course, also be used.

The various additional features of the above-described methods can be further elaborated as following.

1. The Substrate

The substrate can be any glass, polymer or silica, porous or nonporous, substrate. These substrates may contain optionally provided linker molecules thereon. The linker molecules may each include a protecting group. In light-directed polymer synthesis, the protecting group is a photocleavable (photoreactive) protecting group. Many of the glass, polymer and other types of substrates have been described in the above-referenced Patents, which are hereby incorporated by reference. In addition, the porous silica substrates that have been described in the copending application Ser. No. 60/128,402, filed Apr. 8, 1999, incorporated by reference, can also be used in practicing the present invention.

2. Photocleavable Protective Groups

The protective group is preferably on the distal or terminal end of the linker molecule opposite the substrate. The protective group may be either a negative protective group (i.e., the protective group renders the linker molecules less reactive with a monomer upon exposure) or a positive protective group (i.e., the protective group renders the linker molecules more reactive with a monomer upon exposure). In the case of negative protective groups an additional step of reactivation will be required. In some embodiments, this will be done by heating.

The protecting groups are selectively removed from the surface by applying a specific activator, such as electromagnetic radiation of a specific wavelength and intensity. In this case, the protective groups are called photoactivatable protecting groups. Alternatively, chemical deprotection in the vapor or solution phase, using agents such as trichloroacetic acid, trifluoroacetic acid or hydrochloric acid, may be feasible.

The properties and uses of photoreactive protecting compounds have been reviewed. See, McCray et al., *Ann. Rev. of Biophys. and Biophys. Chem.*, 18:239–270 (1989), which is incorporated herein by reference. Preferably, the photocleavable protecting groups will be removable by radiation in the ultraviolet (UV) or visible portion of the electromagnetic spectrum. More preferably, the protecting groups will be removable by radiation in the near UV or visible portion of the spectrum. In some embodiments, however, activation may be performed by other methods such as localized heating, electron beam lithography, laser pumping, oxidation or reduction with microelectrodes, and the like.

Sulfonyl compounds are suitable reactive groups for electron beam lithography. Oxidative or reductive removal is accomplished by exposure of the protecting group to an electric current source, preferably using microelectrodes directed to the predefined regions of the surface which are desired for activation. Other methods may be used in light of this disclosure.

Many, although not all, of the photoremovable protecting groups will be aromatic compounds that absorb near-UV and visible radiation. Suitable photoremovable protecting groups are described in, for example, McCray et al., Patchornik, *J. Amer. Chem. Soc.*, 92:6333 (1970), and Amit et al., *J. Org. Chem.*, 39:192 (1974), which are incorporated herein by reference.

Some classes of photoremovable protecting groups include 6-nitroveratryl (NV), 6-nitropiperonyl (NP), methyl-6-nitroveratryl (MeNV), methyl-6-nitropiperonyl (MeNP), and 1-pyrenylmethyl (PyR), which are used for protecting the carboxyl terminus of an amino acid or the hydroxyl group of a nucleotide, or a saccharide, for example. 6-nitroveratryloxycarbonyl (NVOC), 6-nitropiperonyloxycarbonyl (NPOC), methyl-6-nitroveratryloxycarbonyl (MeNVOC), methylnitropiperonyloxycarbonyl, and 1-pyrenylmethyloxycarbonyl (PyROC), which are used to protect the amino terminus of an amino acid are also preferred. Clearly, many photosensitive protecting groups are suitable for use in the present invention.

Several novel photoremovable protecting groups belonging to 5'-O-pyrenylmethyloxy carbonyl (PYMOC) and to methylnitropiperonyloxycarbonyl have been described in U.S. Pat. No. 6,022,963 (McGall and Nam, inventors), incorporated herein by reference in its entirety for all purposes.

In one aspect, the protecting groups are attached to another moiety to form a compound that will be deprotected, such as a protected monomer. In one aspect, the compound to be deprotected is a 5'-X-2'-deoxythymidine 2-cyanoethyl 3'-N,N-diisopropylphosphoramidite, wherein X may represent the following photolabile protecting groups: ((α-methyl-2-nitropiperonyl)-oxy)carbonyl (MeNPOC), ((Phenacyl)-oxy)carbonyl (PAOC), O-(9-phenylxanthen-9-yl) (PIXYL), and ((2-methylene-9,10-anthraquinone)-oxy)carbonyl (MAQOC). Various methods for generating protected monomers have been described by the U.S. Pat. No. 5,744, 305, which is incorporated by reference. Detailed methods for using photoremovable protecting groups are described in the U.S. Pat. No. 5,424,186, which is also hereby incorporated by reference.

Use of photoremovable protecting groups during solid-phase synthesis of peptides is well known in the art. The formation of peptides on a solid-phase support requires the stepwise attachment of an amino acid to a substrate-bound growing chain. In order to prevent unwanted polymerization of the monomeric amino acid under the reaction conditions, protection of the amino terminus of the amino acid is required.

After the monomer is coupled to the end of the peptide, the N-terminal protecting group is removed, and another amino acid is coupled to the chain. This cycle of coupling and deprotecting is continued for each amino acid in the peptide sequence. See Merrifield, *J. Am. Chem. Soc.*, 85:2149 (1963), and Atherton et al., "Solid Phase Peptide Synthesis" 1989, IRL Press, London, both incorporated herein by reference. Detailed description of peptide synthesis using N-carboxy-end-protected amino acids has been provided by the U.S. Pat. Nos. 5,770,456 and 5,489,678, 5,491,071, 5,424,186, 5,412,087, 5,143,854 and 5,405,783, which are incorporated herein by reference. Use of urethane-protected amino acids having photoremovable protecting groups is also detailed in those Patents.

In a preferred embodiment, the invention herein is used in the synthesis of nucleic acids. Use of photoremovable groups during solid-phase synthesis of nucleic acids is also well known. See U.S. Pat. No. 5,445,934 for a detailed description. The formation of nucleic acids on a solid-phase support requires the stepwise attachment of a nucleotide to a substrate-bound growing nucleotide chain. In order to prevent unwanted polymerization of the monomeric nucleotide under the reaction conditions, protection of the 5'-hydroxyl group of the nucleotide is required.

After the monomer is coupled to the end of the oligomer, the 5'-hydroxyl protecting group is removed, and another nucleotide is coupled to the chain. This cycle of coupling and deprotecting is continued for each nucleotide in the chain. See Gait, "Oligonucleotide Synthesis: A Practical Approach" 1984, IRL Press, London, incorporated herein by reference. As described above, the use of a photoremovable protecting group allows removal, via patterned irradiation, of selected portions of the substrate surface during the deprotection cycle of the solid phase synthesis. This selectively allows spatial control of the synthesis—the next nucleotide is coupled only to the irradiated areas.

Nucleotide polymer synthesis generally involves coupling an activated phosphorous derivative on the 3'-hydroxyl group of a nucleotide with the 5'-hydroxyl group of a nucleotide chain bound to the porous silica solid support. Two major chemical methods exist to perform this coupling: the phosphate-triester and phosphoramidite methods (See Gait, supra.). Protecting groups of the present invention are suitable for use in either method.

Other than the use of photoremovable protecting groups, the nucleoside coupling chemistry is very similar to that used routinely today for oligonucleotide synthesis. These steps include deprotection in the presence of a sensitizing agent, coupling, and oxidation of a solid phase DNA synthesis method. A preferred photoremovable protecting group is PAOC or PIXYL. In some cases, MeNPOC can also be used. A preferable sensitizing agent is dMA. In some aspects, the preferred concentration of dMA is about 10 mM.

Some exemplary nucleoside building blocks are: 5'-PAOC-thymidine-3'-OCEP; 5'-PAOC-$N^4$-t-butylphenoxyacetyl-deoxycytidine-3'-OCEP; 5'-PAOC-$N^4$-t-butylphenoxyacetyl-deoxyguanosine-3'-OCEP; 5'-PAOC-$N^4$-t-butyl-phenoxyacetyl deoxyadenosine-3'-OCEP; 5'-PIXYL-thymidine-3'-OCEP; 5'-PIXYL-$N^4$-t-butylphenoxyacetyl-deoxycytidine-3'-OCEP; 5'-PIXYL-$N^4$-t-butylphenoxyacetyl-deoxyguanosine-3'-OCEP; 5'-PIXYL-$N^4$-t-butyl-phenoxyacetyl deoxyadenosine-3'-OCEP; 5'-MeNPOC-thymidine-3'-OCEP; 5'-MeNPOC-$N^4$-t-butylphenoxyacetyl-deoxycytidine-3'-OCEP; 5'-MeNPOC-$N^4$-t-butylphenoxyacetyl-deoxyguanosine-3'-OCEP; and 5'-MeNPOC-$N^4$-t-butyl-phenoxyacetyl deoxyadenosine-3'-OCEP.

Similar to the methods described in connection with peptide and nucleic acid synthesis, polysaccharide arrays can be synthesized. Since a saccharide typically contains one or more hydroxyl groups, the photolabile protecting groups can be easily attached to one of the free hydroxyl groups. For detailed description of polysaccharide array synthesis, see U.S. Pat. No. 5,424,186, which is hereby incorporated by reference.

In addition to the above-described references, photocleavable protecting groups and methods of using such photocleavable protecting groups for polymer synthesis have been described in U.S. Pat. No. 6,022,963, and in pending application Ser. No. 08/812,005 (filed Mar. 5, 1997), both incorporated by reference herein.

3. Deprotection in the Presence of a Sensitizing Agent and Addition

Photodeprotection is effected by illumination of the substrate through, for example, a mask wherein the pattern has transparent regions with dimensions of, for example, less than 1 cm$^2$ to 10$^{-10}$ cm$^2$. Thus, the regions can be between about 10×10 μm and 500×500 μm. The masks can be arranged to produce a checkerboard array of polymers, although any one of a variety of geometric configurations may be utilized.

The protecting groups of this invention are typically removed by photolysis, i.e., by irradiation, though in selected cases it may be advantageous to use acid or base catalyzed cleavage conditions. Generally irradiation is at wavelengths greater than about 340 nm, preferably at about 365 nm. The photolysis is usually conducted in the presence of hydroxylic or protic solvents, such as aqueous, alcoholic or mixed aqueous-alcoholic or mixed aqueous-organic solvent mixtures. Alcoholic solvents frequently used include methanol and ethanol. The photolysis medium may also include nucleophilic scavengers such as hydrogen peroxide. Photolysis is frequently conducted at neutral or basic pH.

The removal rate of the protecting groups depends on the wavelength and intensity of the incident radiation, as well as the physical and chemical properties of the protecting group itself. Preferred protecting groups are removed at a faster rate and with a lower intensity of radiation. For example, at a given set of conditions, MeNVOC, MeNPOC, PAOC and PIXYL are photolytically removed from the N-terminus of a peptide chain faster than their unsubstituted parent compounds.

In the present invention, deprotection of photocleavable protecting groups is performed in the presence of one or more sensitizing agents. These sensitizing agents are known in the art. In one aspect, the sensitizing agent is a polyaromatic and or heteroatom-containing sensitizer such as 9,10-dimethylanthracene (dMA) and 9-methylcarbazole. In a preferred aspect, the sensitizing agent is dMA and is present at about 10 mM. In a particularly preferred aspect, the sensitizing agent is dMA, the photocleavable protecting group is PAOC or PIXYL. It has been discovered surprisingly that a mixture of PAOC and dMA or PIXYL and dMA provides some of the most desirable photolysis rates and quantitative yields with fewer highly reactive byproducts.

In further aspects, the efficiency of photolysis may be improved by carrying out the photolysis in the presence of nucleophilic solvents such as methanol or water. When advantageous, the photolysis can be carried out with a sensitizing agent, with or without the nucleophilic solvent.

After deprotection, a first of a set of building blocks, each bearing a photolabile protecting group is exposed to the surface of the substrate and it reacts with regions that were addressed by light in the preceding step. The substrate is then illuminated through a second mask which activates another region for reaction with a second protected building block. The pattern of masks used in these illuminations and the sequence of reactants define the ultimate products and their locations, resulting in diverse sequences at predefined locations. The invention takes advantage of combinatorial masking strategies to form a large number of compounds in a small number of chemical steps.

The predefined regions on the substrate can have a surface area of between about 1 $cm^2$ and $10^{-8}$ $cm^2$. In one example, the regions are about 10×10 µm. The substrate, the area of synthesis, and the area for synthesis of each individual polymer could be of any size or shape. For example, squares, ellipsoids, rectangles, triangles, circles, or portions thereof, along with irregular geometric shapes may be utilized. Duplicate synthesis areas may also be applied to a single substrate for purposes of redundancy.

The invention provides an ordered method for forming a plurality of polymer sequences on a porous silica substrate by sequential addition of reagents comprising the step of serially protecting and deprotecting portions of the plurality of polymer sequences for addition of other portions of the polymer sequences. The sequential addition can be accomplished by a number of means, including a binary synthesis strategy.

4. Binary Synthesis Strategy

In a binary synthesis strategy, the substrate is irradiated with a first mask, exposed to a first building block, irradiated with a second mask, exposed to a second building block, etc. Each combination of masked irradiation and exposure to a building block is referred to herein as a "cycle."

In one binary masking scheme, the masks for each cycle allow irradiation of half of a region of interest on the substrate and protection of the remaining half of the region of interest. By "half" it is intended herein not to mean exactly one-half the region of interest, but instead a large fraction of the region of interest such as from about 30 to 70 percent of the region of interest. It will be understood that the entire masking scheme need not take a binary form; instead non-binary cycles may be introduced as desired between binary cycles.

In one example of the binary masking scheme, a given cycle illuminates only about half of the region which was illuminated in a previous cycle, while protecting the remaining half of the illuminated portion from the previous cycle. Conversely, in such preferred embodiments, a given cycle illuminates half of the region which was protected in the previous cycle and protects half the region which was protected in a previous cycle.

Of course, compounds formed in a light-activated synthesis can be positioned in any defined geometric array. A square or rectangular matrix is convenient but not required. The rows of the switch matrix may be transformed into any convenient array as long as equivalent transformations are used for each row.

5. Flow Channel or Spotting Methods

Additional methods applicable to library synthesis on a single substrate are described in U.S. Pat. Nos. 5,677,195, 5,384,261, and 6,040,138 incorporated herein by reference for all purposes. In the methods disclosed in these applications, reagents are delivered to the substrate by either (1) flowing within a channel defined on predefined regions or (2) "spotting" on predefined regions. However, other approaches, as well as combinations of spotting and flowing, may be employed. In each instance, certain activated regions of the substrate are mechanically separated from other regions when the monomer solutions are delivered to the various reaction sites. One of ordinary skill in the art would also appreciate that this method can also be used to deposit pre-synthesized oligomers or polymers for further polymerization.

The "spotting" methods of preparing arrays of the present invention can be implemented in much the same manner as the flow channel methods. For example, a monomer A can be delivered to and coupled with a first group of reaction regions which have been appropriately activated. Thereafter, a monomer B can be delivered to and reacted with a second group of activated reaction regions. Unlike the flow channel embodiments described above, reactants are delivered by directly depositing (rather than flowing) relatively small quantities of them in selected regions. In some steps, of course, the entire substrate surface can be sprayed or otherwise coated with a solution. In preferred embodiments, a dispenser moves from region to region, depositing only as much monomer as necessary at each stop. Typical dispensers include a micropipette, a quill, or a pin and ring to deliver the polymer solution to the substrate and a robotic system to control the position of the micropipette with respect to the substrate, or an ink-jet printer. In other embodiments, the dispenser includes a series of tubes, a manifold, an array of pipettes, or the like so that various reagents can be delivered to the reaction regions simultaneously.

6. Pin-Based Methods

Another method that is useful for the preparation of compounds and libraries of the present invention involves "pin based synthesis." This method is described in detail in U.S. Pat. No. 5,288,514, previously incorporated herein by reference. The method utilizes a substrate having a plurality of pins or other extensions. The pins are each inserted simultaneously into individual reagent containers in a tray. In a common embodiment, an array of 96 pins/containers is utilized.

Each tray is filled with a particular reagent for coupling in a particular chemical reaction on an individual pin. Accordingly, the trays will often contain different reagents. Since the chemistry disclosed herein has been established such that a relatively similar set of reaction conditions may be utilized to perform each of the reactions, it becomes possible to conduct multiple chemical coupling steps simultaneously. In the first step of the process the invention provides for the use of substrate(s) on which the chemical coupling steps are conducted. The substrate is optionally provided with a spacer having active sites. In the particular case of oligonucleotides, for example, the spacer may be selected from a wide variety of molecules which can be used in organic environments associated with synthesis as well as aqueous environments associated with binding studies. Examples of suitable spacers are polyethyleneglycols, dicarboxylic acids, polyamines and alkylenes, substituted with, for example, methoxy and ethoxy groups.

Additionally, the spacers will have an active site on the distal end. The active sites are optionally protected initially by protecting groups. Among a wide variety of protecting groups which are useful are FMOC, BOC, t-butyl esters, t-butyl ethers, and the like. Various exemplary protecting groups are described in, for example, Atherton et al., "Solid Phase Peptide Synthesis," IRL Press (1989), incorporated herein by reference. In some embodiments, the spacer may provide for a cleavable function by way of, for example, exposure to acid or base.

7. Bead Based Methods

A general approach for bead based synthesis is described in U.S. Pat. Nos. 5,770,358, 5,639,603, and 5,541,061 the disclosures of which are incorporated herein by reference. For the synthesis of molecules such as polynucleotides on beads, a large plurality of beads are suspended in a suitable carrier (such as water) in a container. The beads are provided with optional spacer molecules having an active site. The active site is protected by an optional protecting group.

In a preferred embodiment, the beads are tagged with an identifying tag which is unique to the particular double-stranded polynucleotide or probe which is present on each bead. A complete description of identifier tags for use in synthetic libraries is provided in U.S. Pat. No. 5,639,603.

8. Linker Molecules

The linker molecules can be any of those molecules described supra and preferably should be about 4 to about 40 atoms long to provide sufficient exposure. The linker molecules may be, for example, aryl acetylene, ethylene glycol oligomers containing 2–10 monomer units, diamines, diacids, amino acids, among others, and combinations thereof. Alternatively, the linkers may be the same molecule type as that being synthesized (i.e., nascent polymers), such as oligonucleotides or oligopeptides.

The linker molecules or substrate itself and monomers used herein are provided with a functional group to which is bound a protective group. Preferably, the protective group is on the distal or terminal end of the linker molecule opposite the substrate. The protective group may be either a negative protective group (i.e., the protective group renders the linker molecules less reactive with a monomer upon exposure) or a positive protective group (i.e., the protective group renders the linker molecules more reactive with a monomer upon exposure). In the case of negative protective groups an additional step of reactivation will be required. In some embodiments, this will be done by heating.

9. Applying Barrier Layer

The present method may also include a step of applying a barrier layer overlying at least a portion of the linker molecule layer. The barrier layer shields the underlying portion from contact with a reagent capable of otherwise reacting with the underlying portion and applied subsequent to application of the barrier layer, thereby substantially precluding a predetermined chemical reaction from occurring on areas of the substrate overlaid with the barrier material. The applying step forms selected exposed regions of the linker molecule layer (e.g., regions not overlaid with the barrier material), which exposed regions of the linker molecule layer will be deprotected using a reagent.

The barrier pattern can be made of any suitable material capable of masking certain regions of the linker molecule layer to protect such regions from subsequent processing. The barrier pattern may include, for example, materials such as a lacquer, an oil, a mask stencil, a silicone mask, an epoxy, a silicone oil, a polyester, a silicon membrane mask, a liquid capable of providing a barrier to protecting groups, a solid capable of providing a barrier to protecting groups, among others, and combinations thereof. The lacquer may include a lacquer such as Pactra 63-1 and others, often having characteristics formulated to withstand hot fuel. An epoxy may include any suitable epoxy type material such as West 105 and others. Selected oils are a rotary pump oil such as Mowioc MC110, a silicone oil such as Dow Corning 704, and others. Polyester type materials may include TAP SB and the like, and combinations thereof.

The barrier pattern is applied as a liquid or a vapor by a variety of techniques. Examples of selected ways to apply the barrier material include brush, spray techniques, selected printing techniques, and others. Selected printing techniques may be used for the application of liquid barrier materials. The selected techniques of printing include a relief or letterpress (the oldest form), gravure or intaglio, stencil printing, lithography, photoresist, among others.

After optionally deprotecting the linker molecule layer, the barrier material can be then stripped by methods of wet chemical strip, acetone, IPA, and others. The linker molecule layer is then washed or otherwise contacted with a first monomer layer. The first monomer reacts with the activated functional groups of the linker molecules that have been deprotected. The sequence of steps may be repeated to achieve the desired sequence of monomers at selected regions to form an array of oligonucleotides, peptides, other polymers, and the like.

Specific techniques of printing include relief or letterpress, gravure or intaglio, stencil printing, photoresist and lithography, respectively. Each of these techniques may be used for the application of a barrier material, a carrier material, a deprotecting agent, or a polymer unit pattern onto a substrate. More recent forms of printing include xerography (which includes laser printing), ink jet printing (or print medium jet printing), and others. The print medium jet type printer may deliver a pattern of selected print medium in a single pass. A resolution of such printing technique can be as low as about 200 microns and less.

The method can also be practiced using a drop-on-demand printhead. The drop-on-demand printhead has the capability of delivering controlled amounts of fluids such as barrier medium, carrier material, monomer units, and the like onto the surface of a workpiece.

Additional types of printing include a rotary press type printing, gravure offset printing by way of gravure offset printing, features sizes down to about 30 micrometers can be made. Other printing techniques are illustrated in the U.S. Pat. No. 5,599,695, which is incorporated by reference.

Alternatively, a method of applying a medium in selected regions of the substrate is provided. The medium consists of an element selected from a group consisting of a barrier material, a receptor, a deprotection agent, a monomer group, a carrier material, and an activator to selected regions of the substrate top surface.

10. Polymer Formation

After deprotecting, the barrier material will be stripped, for example, by using acetone and polymer synthesis will be accomplished as follows. The method employs a monomer addition cycle wherein monomers are added repetitively to the linker molecule in the first step or to the growing chain (nascent chain) of the polymer in the subsequent steps concomitantly with a series of protection and deprotection steps.

In general, a masking step is used whereby a spatially distributed barrier material is applied to a substrate to block at least one step of a monomer addition cycle from occurring on a portion of the substrate overlaid by the barrier material. In the monomer addition cycle, a monomer unit is covalently linked only to the exposed nascent polymer or linker, whereas other portions of the substrate are overlaid with the barrier material. By repetitive protection, deprotection and monomer addition, polymer elongation occurs.

Thus, the reagents to be applied in a monomer addition cycle would be a monomer (e.g., a nucleotide, nucleoside, nucleoside derivative, amino acid, and the like), a deprotecting agent for removing protecting group(s) which block polymer elongation (e.g., removal of DMT groups by acid hydrolysis), a coupling agent (e.g., phosphoramidites, such as cyanoethyl phosphoramidite nucleosides), a capping agent (e.g., acetic anhydride and 1-methylimidazole), and/or an oxidation agent (e.g., iodine; such as in iodine:water: pyridine:tetrahydrofuran mixture).

Subsequent to the application of the barrier material, the reagent(s) is/are applied and permitted to chemically react with the unshielded portion of the substrate for a suitable time period and under suitable reaction conditions. Following reaction of the unshielded portion with the reagent(s), monomer addition is completed and the barrier material is removed (not necessarily in that order), resulting in a monomer addition to polymer(s) in the unshielded portion of the substrate and substantial lack of monomer addition to polymer(s) in the shielded portion of the substrate, during said monomer addition cycle.

The masking step, wherein a barrier material is applied to a spatially defined portion of the substrate and used to shield said spatially defined portion to block a monomer addition cycle on said spatially defined portion, can be employed repetitively. A first barrier mask is applied to overlay a first spatially defined portion of a substrate creating: (1) a first shielded portion overlain by said barrier mask, and (2) a first unshielded portion comprising the portion of the substrate not overlain by said barrier mask. The application of the first barrier mask is followed by completion of a first monomer addition cycle, whereby a monomer unit is covalently added to the first unshielded portion to extend or initiate a nascent polymer bound to the substrate, typically covalently.

The first barrier mask is removed, concomitant with, prior to, or subsequent to the completion of said first monomer addition cycle, and one or more subsequent cycles of applying a subsequent barrier mask, which may overlay subsequent shielded portions which is/are spatially distinct from said first shielded portion, and performing at least one subsequent monomer addition cycle(s) follows after each cycle by barrier removal, and optionally, a barrier mask is reapplied and a further monomer addition cycle is reinitiated until polymers of a predetermined length (number of incorporated monomer units) are produced. The cycle can be repeated several hundred or thousands or hundreds of thousands of times as desired.

The pattern of barrier material applied in each cycle may be different that the prior or subsequent cycle(s), if any, or may be the same. Often, in the monomer addition cycle, at least one reagent necessary for completion of a monomer addition cycle is applied in vapor phase. Further details may be found in the U.S. Pat. No. 5,599,695, which is incorporated by reference.

The above methodology can be applied to the synthesis of any polymer, including those of biological interest such as polynucleotides, nucleic acids, polypeptides, proteins, oligosaccharides and polysaccharides. Chemical synthesis of polypeptides is known in the art and are described further in Merrifield, J., *J. Am. Chem. Soc.,* 91: 501 (1969); Chaiken I. M., *CRC Crit. Rev. Biochem.,* 11: 255 (1981); Kaiser et al., *Science,* 243:187 (1989); Merrifield, B., *Science,* 232:342 (1986); Kent, S. B. H., *Ann. Rev. Biochem.,* 57: 957 (1988); and Offord, R. E., *Semisynthetic Proteins*, Wiley Publishing (1980)), which are all incorporated herein by reference. In addition, methods for chemical synthesis of peptide, polycarbamate, and oligonucleotide arrays have been reported (see Fodor et al., *Science,* 251:767–773 (1991); Cho et al., *Science,* 261:1303–1305 (1993), each of which is incorporated herein by reference).

The U.S. Pat. No. 5,527,681, the disclosure of which is incorporated herein, describes use of computer tools for forming arrays. For example, a computer system may be used to select nucleic acid or other polymer probes on the substrate, and design the layout of the array as described in U.S. Pat. No. 5,571,639, the disclosure of which is incorporated herein.

11. Data Collection

Devices to detect regions of a substrate which contain fluorescent markers are known in the art. See e.g., the U.S. Pat. Nos. 5,631,734, and 5,744,305, incorporated by reference. This device would be used, for example, to detect the presence or absence of a labeled receptor such as an antibody which has bound to a synthesized polymer on a substrate.

Light is directed at the substrate from a light source such as a laser light source of the type well known to those of skill in the art such as a model no. 2025 made by Spectra Physics. Light from the source is directed at a lens which is preferably a cylindrical lens of the type well known to those of skill in the art. The resulting output from the lens is a linear beam rather than a spot of light, resulting in the capability to detect data substantially simultaneously along a linear array of pixels rather than on a pixel-by-pixel basis.

A detector detects the amount of light fluoresced from the substrate as a function of position. The detector can be a linear CCD array of the type commonly known to those of skill in the art. The x-y translation stage, the light source, and the detector are all operably connected to a computer for control of the device and data collection from the CCD array.

In operation, the substrate is appropriately positioned by the translation stage. The light source is then illuminated, and intensity data are gathered with the computer via the detector.

12. Data Analysis

Methods for analyzing various aspects of the present invention have been disclosed previously. See for example, U.S. Pat. No. 5,445,934, which describes methods for determining the number of molecules per unit area. Briefly, the output from the data collection system is an array of data indicative of fluorescent intensity versus location on the substrate. In general, within any area in which a given polymer has been synthesized, a large number of fluorescence data points are collected.

A plot of number of pixels versus intensity for a scan of a cell when it has been exposed to, for example, a labeled antibody will typically take the form of a bell curve. The data are corrected for removal of these spurious data points, and an average of the data points is thereafter utilized in determining relative binding efficiency.

For each cell, a main data analysis loop is then performed. For each cell, the system calculates the total intensity or number of pixels for the bandwidth centered around varying intensity levels.

The system then integrates the data within the bandwidth for each of the selected cells, sorts the data using the synthesis procedure file, and displays the data to a user on, for example, a video display or a printer.

While the above methods and examples are provided for illustrative purposes only, one of ordinary skill in the art would understand that a number of alternative devices and methods are available to detect, collect and analyze polymer synthesis data. Any such art-recognized equivalent methods can be easily applied to practice the above-described invention.

13. Scope of the Invention

The above-described methods have a number of applications, including the array synthesis of any polymer. Thus, array synthesis of polymers such as both linear and cyclic polymers of nucleic acids, polysaccharides, phospholipids, and peptides having either α-, β-, or ω-amino acids, heteropolymers in which a known drug is covalently bound to any of the above, polyurethanes, polyesters, polycarbonates, polyureas, polyethyleneimines, polyamides, polyarylene sulfides, polysiloxanes, polyimides, polyacetates, or other polymers which will be apparent upon review of this disclosure are within the scope of this invention.

Further understanding of the nature and advantages of the inventions herein may be realized by reference to the remaining portions of the specification and the attached drawings.

APPLICATIONS

The above-described arrays of polymers such as polypeptides, or nucleic acids or polysaccharides prepared on the substrates can be used in a variety of applications including biological binding assays including nucleic acid hybridization assays.

Polynucleotide or nucleic acid probes have long been used to detect complementary nucleic acid sequences in a nucleic acid of interest (the "target" nucleic acid). In some assay formats, the nucleotide polymer probe is tethered, i.e., by covalent attachment, to a solid support, and arrays of nucleotide polymer probes immobilized on solid supports have been used to detect specific nucleic acid sequences in a target nucleic acid. See, e.g., PCT patent publication Nos. WO 89/10977 and 89/11548.

One general method of hybridization of DNA targets to the probe arrays is as follows. The porous silica substrate is placed in a bath of fluorescein-labeled DNA target solution at room temperature with gentle stirring. Hybridization is allowed to proceed for up to two days with intermediate data points taken. To scan the slides, the wet chips are removed from the bath and kept in contact with buffer solution during the scan. Scans are performed on a specially constructed scanning laser confocal fluorescence microscope, which employs excitation with a 488 nm argon laser focused on the substrate surface. Emitted light is collected through confocal optics with photon-counting electronics. The data is thus collected and analyzed as provided in, for example, the U.S. Pat. Nos. 5,631,734, 5,510,270 and 5,324,633, the disclosure of which are incorporated herein.

A variety of methods can be used to enhance detection of labeled targets bound to a probe on the array. In one embodiment, the protein MutS (from *E. coli*) or equivalent proteins such as yeast MSH1, MSH2, and MSH3; mouse Rep-3, and *Streptococcus* Hex-A, is used in conjunction with target hybridization to detect probe-target complex that contain mismatched base pairs. The protein, labeled directly or indirectly, can be added to the chip during or after hybridization of target nucleic acid, and differentially binds to homo- and heteroduplex nucleic acid. A wide variety of dyes and other labels can be used for similar purposes. For instance, the dye YOYO-1 is known to bind preferentially to nucleic acids containing sequences comprising runs of 3 or more G residues.

An improved hybridization signal detection using betaine (N,N,N-trimethylglycine) as an isostabilizing agent is disclosed in U.S. Ser. No. 08/648,709, filed, May 16, 1996, which is hereby incorporated by reference. Betaine can be present at a concentration of about 1M to about 10M, and preferably, at a concentration of about 4M to about 6M.

The probes in hybridization assays can be single stranded or double stranded nucleic acids, polynucleotides or polynucleotides. Further, the hybridization may include a ligation step which increases the hybridization stability thereby improving signal detection. These techniques are illustrated in the copending U.S. Application No. 60/100,393, filed Sep. 15, 1998, which is hereby incorporated by reference.

EXPERIMENTAL

Examples are provided herein, merely to illustrate, but not to limit the scope of, the invention. Some of the examples concern the use of 5'-X-2'-deoxythymidine-2-cyanoethyl-3'-N,N-diisopropylphosphoramidites on a support as photolabile protecting groups in various solvents. In these protecting groups, X may represent the following photolabile groups: ((α-methyl-2-nitropiperonyl)-oxy)carbonyl (MeNPOC), ((Phenacyl)-oxy)carbonyl (PAOC), O-(9-phenylxanthen-9-yl) (PIXYL), and ((2-methylene-9,10-anthraquinone)-oxy)carbonyl (MAQOC).

These photolabile protecting groups have been described in various publications. See for example, Banerjee, A. and Falvet, D. E., *J. Org. Chem.*, 63: 6245–6251 (1997); Banerjee, A. et al., *Tetrahedron Letters*, 39: 4635–4638 (1998); Misetic, A. and Boyd, M. K., *Tetrahedron Letters* 39: 1653–1656 (1998); and Furuta, T. et al., *J. Org. Chem.*, 60: 3953–3956 (1995). Photodeprotection rates were determined in the above experiments, using the methodology of McGall, G. et al., *J. Am. Chem. Soc.* 119:5081–5091 (1997). These methods use discrete exposure times at constant light intensity and a fluorescence coupling step with subsequent scanning analysis to yield psuedo-first order photolysis rate constants.

Solvents were varied and rates of deprotection for the photolabile groups were determined. In addition, the methods also use polyaromatic and or heteroatom containing senitizers such as 9,10-dimethylanthracene and 9-methylcarbazole (available commercially from Aldrich Chemical Co., Milwaukee, Wis.) as added solutes in a given solvent. Further examples illustrate the use of the above reagents to achieve faster photolysis rates. The examples are further illustrated by the synthesis of a polynucleotide array, such as a polythymidine ($T_6$) array. The efficiency of the methods is shown by anion-exchange HPLC analysis.

EXAMPLES

In the following examples, deoxythymidine was functionalized with the photocleavable protecting group, 5'-X-2'-deoxythymidine phosphoramidite, where X is ((α-methyl-2-nitropiperonyl)-oxy)carbonyl (MeNPOC), ((Phenacyl)-oxy)carbonyl (PAOC), O-(9-phenylxanthen-9-yl) (PIXYL), or ((2-methylene-9,10-anthraquinone)-oxy)carbonyl (MAQOC). Methods of preparing these compounds are known in the art. While the functionalized compound in these examples is a 2'-deoxynucleoside, it should be emphasized that other compounds can be similarly functionalized such that polymers other than nucleic acids as described herein can be synthesized.

1. Determination of Photodeprotection Rates

Photodeprotection rates of 5'-X-2'-deoxythymidine phosphoramidites on glass support were evaluated in a variety of solvents with and without the presence of sensitizing reagents such as 9,10-dimethylanthracene (dMA) and 9-methyl carbazole (9MC). Photolysis rates and half-lives were determined as described by McGall et al. In these experiments, MeNPOC was used as a control to compare the rate and quantitative yields of photodeprotection. The efficiency of synthesis was determined by quantitative HPLC analysis as described in the procedure Surface Analysis of VLSIPS Chip by HPLC (DOP AF001).

The photolysis rates and conditions employed for various photogroups are presented in Table 1. In the absence of a solvent, the photolysis of MeNPOC at 35 mW/cm$^2$ had the fastest rate with a $t_{1/2}$ of 11.62 seconds compared to the other protecting groups. Of the solvents, without addition of sensitizers, dioxane yielded the fastest solvent photolysis rate of 10.4 seconds for MeNPOC. The photolysis rates of PAOC were much slower and the fastest reaction was obtained in isopropyl alcohol with a $t_{1/2}$ of 30 seconds. Addition of 9,10-dimethylanthracene (dMA) to the solution during the course of photolysis greatly accelerated the photolysis. dMA ($\lambda$max=398 nm) is a photosensitizing agent, which in the excited state, is a one-electron donor. Solutions of 10 mM dMA gave much better electron transfer and subsequent photo-deprotection than those of 9MC.

The results of photolysis acceleration data are quite unexpected. A solution of 10 mM dMA has provided the fastest photolysis with PAOC, PIXYL and MeNPOC. With a 10 mM concentration of dMA in acetonitrile, the half-lives of MeNPOC, PAOC and PIXYL were 5.28 seconds, 4.8 seconds and 1.47 seconds, respectively.

TABLE 1

Rates of Deprotection of the Photocleavable Protecting Groups Under Various Solvent Conditions

| Protecting Group | Solvent | Avg. Rate | St. Dev. | Avg. Amp | St. Dev. | Half Lives | St. Dev. |
|---|---|---|---|---|---|---|---|
| MeNPOC | Water | 0.02923 | 0.00084 | 8630.8 | 1417.7 | 23.71 | 0.66 |
| MeNPOC | MeOH | 0.03071 | 0.01294 | 9371.8 | 1247.6 | 22.57 | 6.69 |
| MeNPOC | Isoprop. | 0.04475 | 0.00481 | 9569.4 | 933.4 | 15.49 | 1.50 |
| MeNPOC | Dry | 0.05966 | 0.00436 | 8927.9 | 697.8 | 11.62 | 0.79 |
| MeNPOC | Dioxane:Water | 0.04699 | 0.01330 | 10273.6 | 1138.4 | 14.75 | 3.25 |
| MeNPOC | Dioxane | 0.06659 | 0.00395 | 8183.9 | 462.0 | 10.41 | 0.58 |
| MeNPOC | ACN | 0.02847 | 0.00546 | 8175.3 | 1911.1 | 24.35 | 3.92 |
| MeNPOC | 10 mM dMA | 0.11230 | 0.04294 | 8965.4 | 3507.9 | 6.17 | 1.71 |
| MeNPOC | 5 mM dMA | 0.02431 | 0.00642 | 9538.2 | 119.7 | 28.51 | 5.95 |
| MeNPOC | 1 mM dMA | 0.04530 | 0.00374 | 9437.2 | 1747.3 | 15.30 | 1.17 |
| MeNPOC | .1 mM dMA | 0.02677 | 0.00026 | 8268.1 | 68.3 | 25.89 | 0.24 |
| MeNPOC | 10 mM 9 MC | 0.03917 | 0.00166 | 2044.3 | 21.2 | 17.70 | 0.72 |
| MeNPOC | 1 mM 9 MC | 0.03735 | 0.00467 | 2100.2 | 91.2 | 18.56 | 2.06 |
| MeNPOC | .1 mM 9 MC | 0.03491 | 0.00162 | 2024.9 | 98.7 | 19.85 | 0.88 |
| MeNPOC | ACN:Water | 0.02175 | 0.00215 | 7120.1 | 395.1 | 31.87 | 2.86 |
| PAOC | Water | 0.00892 | 0.00470 | 1348.9 | 109.9 | 77.73 | 26.84 |
| PAOC | MeOH | 0.00869 | 0.00189 | 1339.3 | 139.8 | 79.81 | 14.26 |
| PAOC | Isoprop. | 0.02286 | 0.00468 | 1013.1 | 127.4 | 30.32 | 5.16 |
| PAOC | Dry | 0.00444 | 0.00171 | 4139.1 | 1999.9 | 156.03 | 43.43 |
| PAOC | Dioxane:Water | 0.00592 | 0.00081 | 2050.3 | 179.2 | 117.00 | 14.05 |
| PAOC | Dioxane | 0.01951 | 0.00167 | 871.9 | 128.5 | 35.54 | 2.81 |
| PAOC | ACN | 0.01200 | 0.00085 | 1469.8 | 433.0 | 57.76 | 3.80 |
| PAOC | 10 mM dMA | 0.14331 | 0.00240 | 9925.6 | 625.8 | 4.84 | 0.08 |
| PAOC | 5 mM dMA | 0.01875 | 0.00144 | 12992.7 | 1299.2 | 36.96 | 2.64 |
| PAOC | 1 mM dMA | 0.02531 | 0.00140 | 7121.1 | 905.8 | 27.38 | 1.44 |
| PAOC | .1 mM dMA | 0.00957 | 0.00027 | 1337.3 | 8.8 | 72.45 | 1.96 |
| PAOC | 10 mM 9 MC | 0.00519 | 0.00007 | 2973.4 | 134.5 | 133.68 | 1.74 |
| PAOC | 1 mM 9 MC | 0.01110 | 0.00013 | 399.4 | 11.9 | 62.42 | 0.74 |
| PAOC | 1 mM 9 MC | 0.00988 | 0.00035 | 296.3 | 3.8 | 70.18 | 2.39 |
| PIXYL | MeOH | 0.01158 | 0.00261 | 983.5 | 163.9 | 59.85 | 11.00 |
| PIXYL | ACN | 0.02111 | 0.00370 | 677.5 | 70.2 | 32.84 | 4.90 |
| PIXYL | 10 mM dMA | 0.47111 | 0.00104 | 2111.8 | 150.2 | 1.47 | 0.00 |
| PIXYL | Water:acetonitrile | 0.00671 | 0.00080 | 950.0 | 270.7 | 103.29 | 11.05 |
| MAQOC | Diox:Water | 0.01918 | 0.00492 | 1428.0 | 54.1 | 36.13 | 7.37 |
| MAQOC | ACN | 0.05599 | 0.01671 | 1054.4 | 137.6 | 12.38 | 2.84 |
| MAQOC | 10 mM dMA | 0.02898 | 0.01878 | 6666.9 | 3253.0 | 23.91 | 9.40 |

2. Determination of Photodeprotection Yields

Photodeprotection yields were measured for a six-mer array using the procedures described in the literature. The HPLC analysis of the data is displayed in Tables 2–5 and in FIG. 2. Taking the example of a 6-mer DNA synthesis, Table 2 shows that photodeprotection with PAOC in 10 mM dMA at 57 seconds of exposure provided approximately 43% net yield. Table 3 shows that for a 6-mer DNA synthesis, photodeprotection with dry MeNPOC in 10 mM dMA at 65 seconds of exposure resulted in about 11% net yield. Table 4 shows that for a 6-mer DNA synthesis, photodeprotection with dry MeNPOC and in the absence of dMA at a longer exposure of 124 seconds provided about 23% yield. These data are summarized in Table 5.

TABLE 2

PAOC in 10 mM dMA 57 second exposure time
Borofloat-268

| Peak | % Area | Area cpl yield | cpl effec | relative Yield | Yield pmoles | % net Yield |
|---|---|---|---|---|---|---|
|  | 0 |  |  | 0 | 0 | 0 |
| 1-mer | 18.807 | 92.96 |  | 0.18807 | 44.273323 |  |
| 2-mer | 6.965 | 74.153 | 0.7976872 | 0.06965 | 16.396219 | 0.74153 |
| 3-mer | 5.612 | 67.188 | 0.9060726 | 0.05612 | 13.211139 | 0.67188 |
| 4-mer | 7.239 | 61.576 | 0.9164732 | 0.07239 | 17.041239 | 0.61576 |
| 5-mer | 10.874 | 54.337 | 0.882438 | 0.10874 | 25.598347 | 0.54337 |
| 6-mer | 43.463 | 43.463 | 0.7998785 | 0.43463 | 102.3157 | 0.43463 |
| Int Std | 2.104 |  |  |  |  |  |
| total area | 100 |  |  |  |  |  |
| Total pm |  |  |  |  | 218.83597 |  |
| Total psc |  |  |  |  | 133.43657 |  |

TABLE 3

MeNPOC in 10 mM dMA and 65 second exposure time
Borofloat-266

| Peak | % Area | Area cpl yield | cpl effec | relative Yield | Yield pmoles | % net Yield |
|---|---|---|---|---|---|---|
|  | 0 |  |  | 0 | 0 | 0 |
| 1-mer | 19.854 | 75.8361 |  | 0.19854 | 10.081696 |  |
| 2-mer | 10.1111 | 55.9821 | 0.7381986 | 0.101111 | 5.1343324 | 0.559821 |
| 3-mer | 8.141 | 45.871 | 0.8193869 | 0.08141 | 4.133932 | 0.45871 |
| 4-mer | 12.347 | 37.73 | 0.822524 | 0.12347 | 6.2697038 | 0.3773 |
| 5-mer | 14.036 | 25.383 | 0.6727538 | 0.14036 | 7.127364 | 0.25383 |
| 6-mer | 11.347 | 11.347 | 0.4470315 | 0.11347 | 5.7619121 | 0.11347 |
| Int Std | 9.754 |  |  |  |  |  |
| total area | 100 |  |  |  |  |  |
| Total pm |  |  |  |  | 38.50894 |  |
| Total psc |  |  |  |  | 23.481061 |  |

TABLE 4

MeNPOC Dry 124 second exposure time
Sodalime-194

| Peak | Area | Area cpl yield | cpl effec | relative Yield | Yield pmoles | % net Yield |
|---|---|---|---|---|---|---|
|  | 0 |  |  | 0 | 0 | 0 |
| 1-mer | 18.831 | 80.88 |  | 0.18831 | 20.630379 |  |
| 2-mer | 12.743 | 62.049 | 0.7671736 | 0.12743 | 13.960646 | 0.62049 |
| 3-mer | 9.311 | 49.306 | 0.7946301 | 0.09311 | 10.200704 | 0.49306 |
| 4-mer | 7.672 | 39.995 | 0.8111589 | 0.07672 | 8.4050909 | 0.39995 |
| 5-mer | 8.888 | 32.323 | 0.808176 | 0.08888 | 9.7372847 | 0.32323 |
| 6-mer | 23.435 | 23.435 | 0.7250255 | 0.23435 | 25.67431 | 0.23435 |
| Int Std | 4.521 |  |  |  |  |  |
| total area | 100 |  |  |  |  |  |
| Total pm |  |  |  |  | 88.608414 |  |
| Total psc |  |  |  |  | 54.029521 |  |

TABLE 5

Summary of Results: Comparison

|  | PAOC in 10 mM dMA | MeNPOC in 10 mM dMA | MENPOC DRY |
|---|---|---|---|
| 2-mer | 0.797687177 | 0.738198562 | 0.767173591 |
| 3-mer | 0.90607258 | 0.819386911 | 0.79463005 |
| 4-mer | 0.91647318 | 0.822524035 | 0.811158885 |
| 5-mer | 0.882437963 | 0.672753777 | 0.808176022 |
| 6-mer | 0.799878536 | 0.447031478 | 0.725025524 |

Figure 2:
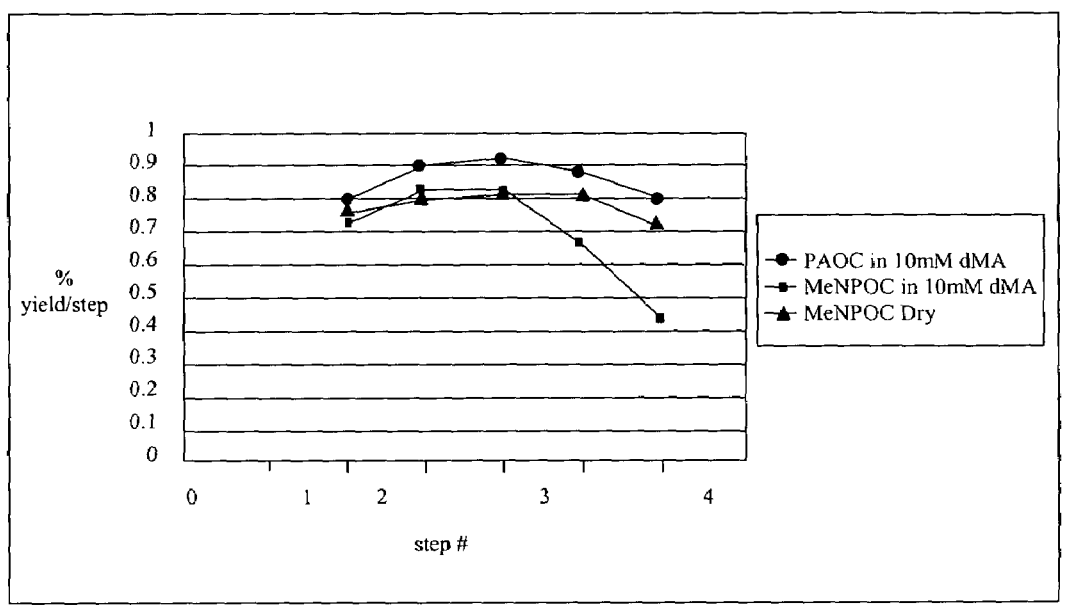
FIG. 2 is a graphical display of coupling efficiency data for up to a hexamer nucleic acid prepared in the presence of various sensitizing conditions, according to the methods of the present invention. The graph shows that PAOC has provided the best yields.

FIG. 2 shows HPLC data for coupling efficiencies of photodeprotections on a PEG-sulfone linker surface. Again, this data show that PAOC in 10 mM dMA provided the highest yield for a six-mer DNA, at about 80%. Thus, these data clearly establish that the best coupling conditions occur for PAOC in 10 mM dMA, providing both a good quantitative photodeprotection yield and a fast rate of deprotection. In contrast, while the addition of dMA during MeNPOC photodeprotection increased the rate of deprotection, it appeared to actually decrease the relative yield (11%). This is a surprising and unexpected result. It should be noted that PAOC deprotection is efficient irrespective of the polymer length.

The above description is illustrative and not restrictive. Many variations of the invention will become apparent to those of skill in the art upon review of this disclosure. The scope of the invention should, therefore, be determined not with reference to the above description, but instead should be determined with reference to the appended claims along with their full scope of equivalents.

What is claimed is:

1. A method for removing a photolabile protecting group attached by a chemical bond to at least one monomer, comprising irradiating said photolabile protecting group in the presence of at least one sensitizer; wherein said monomer is covalently attached to a solid support or a polymer, wherein said monomer is a nucleic acid, nucleotide, or nucleoside, and wherein said sensitizer is 9,10-dimethylanthracene.

2. The method of claim 1, wherein said photolabile protecting group is selected from the group consisting of ((α-methyl-2-nitropiperonyl)-oxy)carbonyl (MeNPOC), ((Phenacyl)-oxy)carbonyl (PAOC), and O-(9-phenylxanthen-9-yl) (PIXYL).

3. The method of claim 1, wherein the monomer is linked to the photolabile protecting group via a hydroxy or amine group.

4. The method of claim 1, wherein the nucleoside is a ribonucleoside or deoxyribonucleoside.

5. The method of claim 4, wherein the ribonucleoside is adenosine, cytidine, uracil, or guanosine.

6. The method of claim 4, wherein the deoxyribonucleoside is deoxyadenosine, deoxycytidine, deoxythymidine, or deoxyguanosine.

7. A method for removing a photolabile protecting group attached by a chemical bond to at least one monomer, comprising irradiating said photolabile protecting group in the presence of at least one sensitizer; wherein said monomer is covalently attached to a solid support, wherein the monomer is a nucleotide; the photolabile group is ((α-methyl-2-nitropiperonyl)-oxy)carbonyl (MeNPOC); and the sensitizer is 9,10-dimethylanthracene.

8. The method of claim 1, wherein irradiating is at wavelengths greater than about 340 nm.

9. The method of claim 8, wherein irradiating is at wavelengths greater than about 365 nm.

* * * * *